United States Patent [19]
Kernan et al.

[11] Patent Number: 5,885,430
[45] Date of Patent: Mar. 23, 1999

[54] CAPILLARY TUBE HOLDER FOR AN ELECTROPHORETIC APPARATUS

[75] Inventors: John R. Kernan, Loganton; Thomas E. Kane, Bellefonte, both of Pa.

[73] Assignee: Spectrumedix Corporation, State College, Pa.

[21] Appl. No.: 726,877

[22] Filed: Oct. 4, 1996

[51] Int. Cl.[6] .......................... G01N 27/26; G01N 27/447
[52] U.S. Cl. .......................... 204/453; 204/451; 204/601; 204/604
[58] Field of Search ...................... 204/601, 602, 204/603, 604, 605, 451, 452, 453, 454, 455; 422/100, 65; 436/180

[56] References Cited

U.S. PATENT DOCUMENTS

| | | | |
|---|---|---|---|
| 5,198,091 | 3/1993 | Burolla et al. | 204/601 |
| 5,274,240 | 12/1993 | Mathies et al. | 204/603 |
| 5,356,525 | 10/1994 | Goodale et al. | 204/604 X |
| 5,413,686 | 5/1995 | Klein et al. | 204/604 X |
| 5,417,925 | 5/1995 | Goodale et al. | 204/452 |
| 5,436,130 | 7/1995 | Mathies et al. | 435/6 |
| 5,498,324 | 3/1996 | Yeung et al. | 204/452 |
| 5,605,666 | 2/1997 | Goodale et al. | 204/603 X |
| 5,730,850 | 3/1998 | Kambara et al. | 204/603 |

FOREIGN PATENT DOCUMENTS

| | | |
|---|---|---|
| 0257855 | 3/1988 | European Pat. Off. . |
| 0723149 | 7/1996 | European Pat. Off. . |
| 9011484 | 10/1990 | Germany . |
| 2113903 | 8/1983 | United Kingdom . |
| 8904966 | 10/1990 | WIPO . |
| 9429712 | 12/1994 | WIPO . |
| 9429713 | 12/1994 | WIPO . |

*Primary Examiner*—Robert J. Warden
*Assistant Examiner*—John S. Starsiak, Jr.
*Attorney, Agent, or Firm*—Pennie & Edmonds LLP

[57] ABSTRACT

An automated electrophoretic system is disclosed. The system employs a capillary cartridge having a plurality of capillary tubes. The cartridge has a first array of capillary ends projecting from one side of a plate. The first array of capillary ends are spaced apart in substantially the same manner as the wells of a microtitre tray of standard size. This allows one to simultaneously perform capillary electrophoresis on samples present in each of the wells of the tray. The capillary cartridge has two embodiments. In one embodiment, the second ends of the capillary tubes are also arranged is such an array. In a second embodiment, the second ends communicate with an interior cavity of pressure cell from which solutions, gels and the like may be introduced. The pressure cell allows for applying high pressure to clean out the capillary tubes. An apparatus for performing automated capillary gel electrophoresis using such a cartridge is also disclosed.

35 Claims, 10 Drawing Sheets

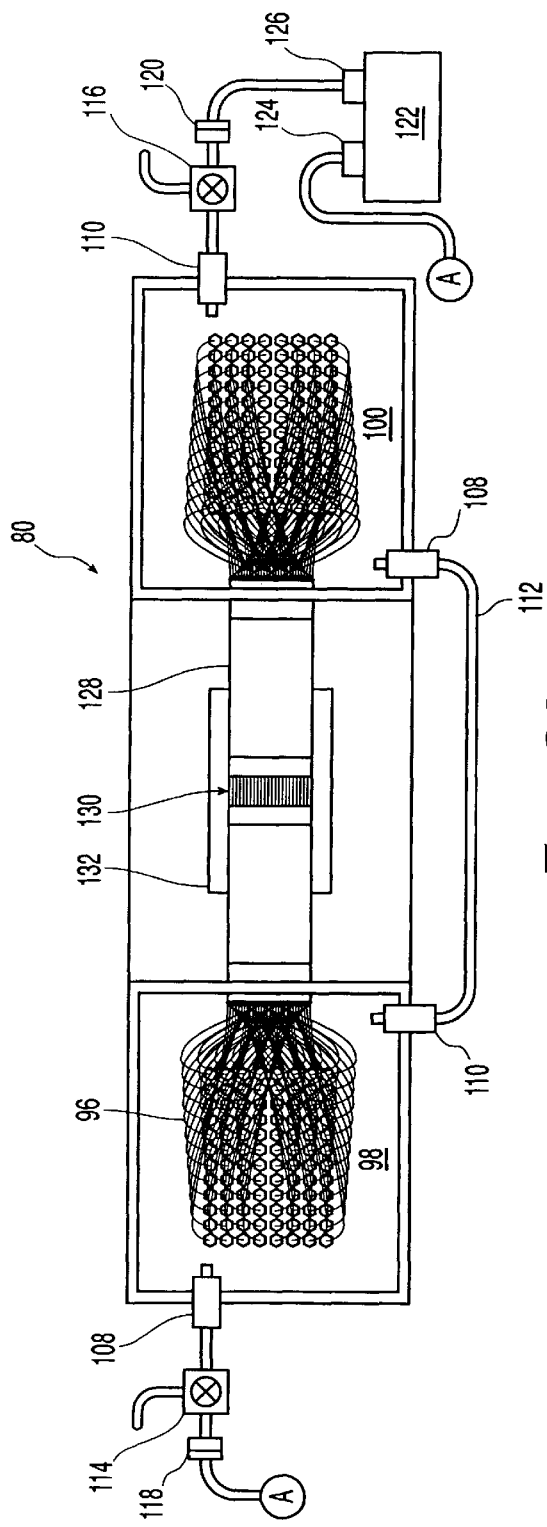
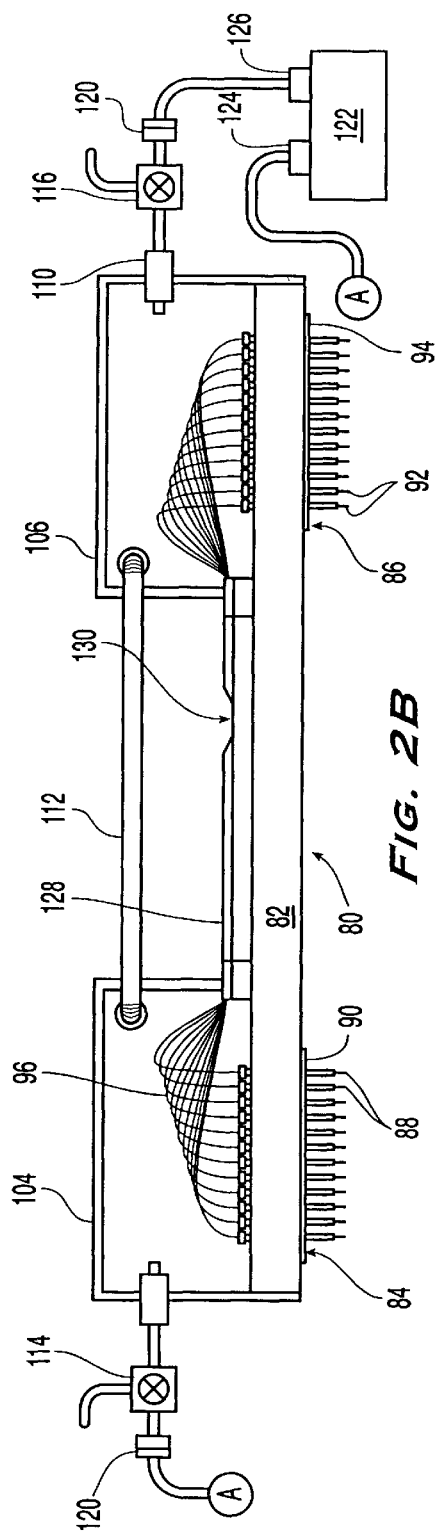
FIG. 2A
FIG. 2B

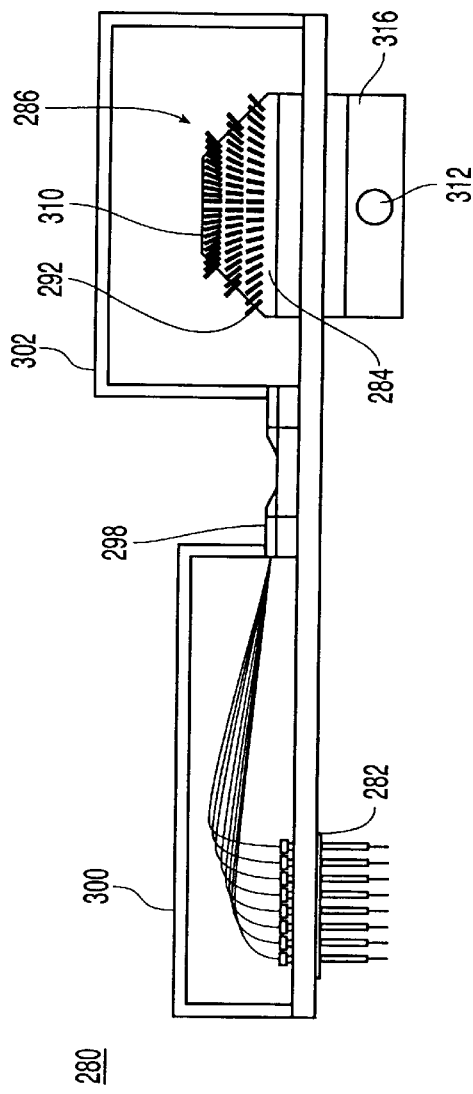
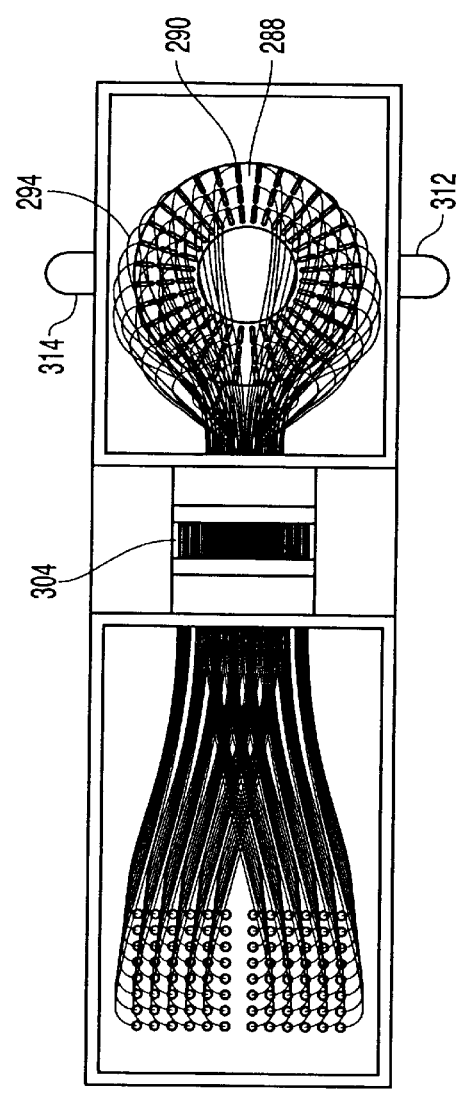
FIG. 6A
FIG. 6B

CAPILLARY TUBE HOLDER FOR AN ELECTROPHORETIC APPARATUS

TECHNICAL FIELD

This invention relates to an apparatus for performing electrophoresis. More particularly, it pertains to an automated electrophoresis system employing capillary cartridges which are configured for use with commercially available, microtitre trays of standard size.

BACKGROUND

Electrophoresis is a well-known technique for separating macromolecules. In electrophoretic applications, molecules in a sample to be tested are migrated in a medium across which a voltage potential is applied. Oftentimes, the sample is propagated through a gel which acts as a sieving matrix to help retard and separate the individual molecules as they migrate.

One application of gel electrophoresis is in DNA sequencing. Prior to electrophoresis analysis, the DNA sample is prepared using well-known methods. The result is a solution of DNA fragments of all possible lengths corresponding to the same total sequential order, with each fragment terminated with a tag label corresponding to the identity of the given terminal base.

The separation process employs a capillary tube filled with conductive gel. To introduce the sample, one end of the tube is placed into the DNA reaction vial. After a small amount of sample enters the capillary end, both capillary ends are then placed in separate buffer solutions. A voltage potential is then applied across the capillary tube. The voltage drop causes the DNA sample to migrate from one end of the capillary to the other. Differences in the migration rates of the DNA fragments cause the sample to separate into bands of similar-length fragments. As the bands traverse the capillary tube, the bands are typically read at some point along the capillary tube using one of several detection techniques.

Usually, multiple DNA preparation reactions are performed in a commercially available microtitre tray having many separate low-volume wells, each holding on the order of 200–1000 micro-liters. The microtitre trays come in standard sizes. In the biotech industry, the currently preferred microtitre tray has a rectangular array comprising of 8 rows and 12 columns of wells. The centers of adjacent wells found in a single row are separated by approximately 0.9 cm, although this figure may vary by one or two tenths of a millimeter. The same holds for the spacing between adjacent wells in a single column. The rectangular array of 96 wells has a footprint within an area less than 7.5 cm×11 cm.

Miniaturization has allowed more wells to be accommodated in a single microtitre tray having the same footprint. New trays having four times the density of wells within the same footprint have already been introduced and are fast becoming the industry standard. Thus, these new trays have 16 rows and 24 columns with an inter-well spacing of approximately 0.45 cm.

It is not uncommon to analyze several thousand DNA samples for a given DNA sequencing project. Needless, to say, it is time consuming to employ a single capillary tube for several thousand runs.

Prior art devices have suggested means for analyzing DNA bands in multiple capillaries simultaneously. Such a device is disclosed in U.S. Pat. No. 5,498,324 to Yeung et al, whose contents are incorporated by reference in their entirety. This reference teaches a means for detecting the DNA bands as they are separated in multiple capillary tubes which are positioned parallel to another. However, in such an arrangement, each capillary tube is filled with gel and a sample is introduced into each capillary tube.

The arrangement described above takes a considerable amount of time to fill each capillary tube with gel. It also takes considerable effort to introduce a reaction sample into one end of each of the tubes reproducibly and reliably.

It is also not uncommon that one uses the same capillary tube for several consecutive sample runs. This, obviously risks cross-contamination of samples, which is a further disadvantage in certain prior art arrangements.

SUMMARY OF THE INVENTION

One object of the invention is to provide a device which allows one to simultaneously introduce samples into a plurality of capillary tubes directly from microtitre trays having a standard size.

Another object of the invention is to provide a device which avoids the risk of contamination from one sample to the next.

Still another object of the invention to provide a device which allows one to clean the capillary tubes and recondition them in an automated fashion.

These objects are achieved by a disposable capillary cartridge which can be cleaned between electrophoresis runs, the cartridge having a plurality of capillary tubes. A first end of each capillary tube is retained in a mounting plate, the first ends collectively forming an array in the mounting plate. The spacing between the first ends corresponds to the spacing between the centers of the wells of a microtitre tray having a standard size. Thus, the first ends of the capillary tubes can simultaneously be dipped into the samples present in the tray's wells. The cartridge is provided with a second mounting plate in which the second ends of the capillary tubes are retained.

Plate holes may be provided in each mounting plate and the capillary tubes inserted through these plate holes. In such case, the plate holes are sealed airtight so that the side of the mounting plate having the exposed capillary ends can be pressurized. Application of a positive pressure in the vicinity of the capillary openings in this mounting plate allows for the introduction of air and fluids during electrophoretic operations and also can be used to force out gel and other materials from the capillary tubes during reconditioning. The capillary tubes may be protected from damage using a needle comprising a cannula and/or plastic tubes, and the like when they are placed in these plate holes. When metallic cannula or the like are used, they can serve as electrical contacts for current flow during electrophoresis.

In one embodiment, the second ends of the capillary tubes are arranged in an array which corresponds to the wells in the microtitre tray. This allows for each capillary tube to be isolated from its neighbors and therefore free from cross-contamination, as each end is dipped into an individual well. Thus, in the first embodiment, the cartridge has two sets of mounting plates/arrays which are substantially the same.

In a second embodiment, the second mounting plate is again provided with plate holes through which the second ends of the capillary tubes project. In the second embodiment, the second mounting plate serves as a pressure containment member of a pressure cell and the second ends of the capillary tubes communicate with an internal cavity of the pressure cell. The pressure cell is also formed with an inlet and an outlet. Gels, buffer solutions, cleaning agents, and the like may be introduced into the internal cavity through the inlet, and each of these can simultaneously enter the second ends of the capillaries.

Both embodiments may also be provided with a window region between the two mounting plates, through which window region one can detect the migration of bands along the capillary tubes. Temperature control means may be provided on either side of the window region, as well. Also, in each embodiment, enclosures may be provided to surround each side of the two mounting plates so as to allow for additional temperature control. These enclosures also protect the operator from the high voltage and high pressure associated with the apparatus. At the same time, the enclosures protect the capillary tubes from mechanical damage.

BRIEF DESCRIPTION OF THE DRAWINGS

FIGS. 2A and 2B are a top and side view, respectively, of one embodiment of a cartridge of the present invention;

FIGS. 6A and 6B are a side and a top view, respectively, of a second embodiment of a cartridge of the present invention;

DETAILED DESCRIPTION OF THE PREFERRED EMBODIMENT

Figure 1:
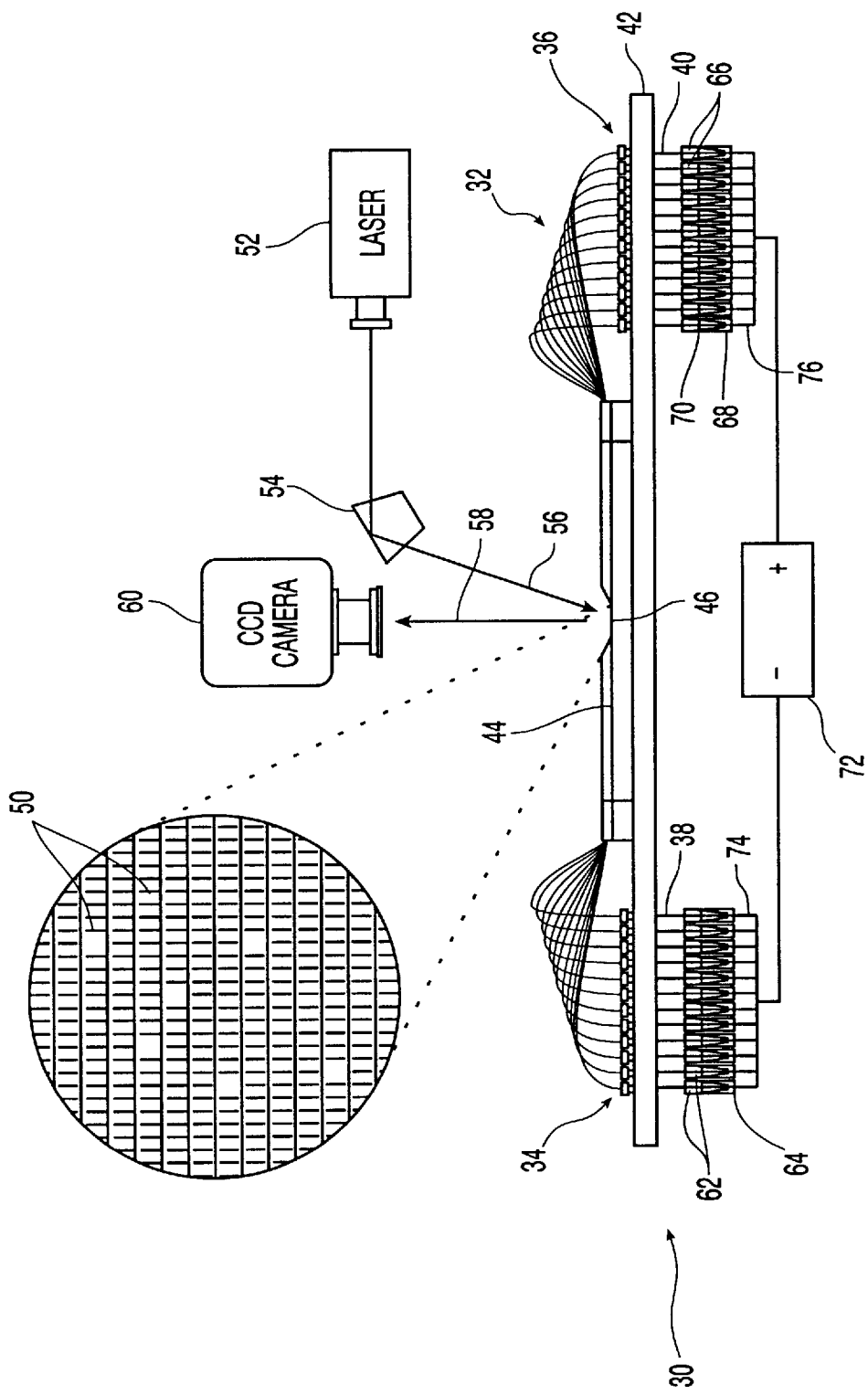
FIG. 1 is a side view of an arrangement in accordance with the present invention.

FIG. 1 presents a schematic illustrating the use of a device in accordance with the present invention. A cartridge 30 of the present invention comprises a plurality of capillary tubes 32 having substantially the same length. The capillary tubes extend between a sample-side connection array 34 and gel side connection array 36. The capillary tubes 32 terminate on the sample-side in an array of first capillary ends 38 and on the gel side in an array of second capillary ends 40.

Thus, both ends of each of the capillary tubes 32 in FIG. 1 extends through individual plate holes in a base member 42, which preferably is formed from polycarbonate, or acrylic or the like. Alternatively, each array of capillary ends may be retained in a separate mounting plate having the plate holes, and each of the mounting plates may then be fixed to a base member. Also, instead of passing each capillary tube through an individual plate hole, one or more capillary tubes may be collected together and sent through a common hole, or even no hole at all.

Between the two arrays, the capillary tubes 32 pass through a thermoelectric element 44 which is mounted on the base member 42. The thermoelectric element is arranged on either side of a window region 46. The thermoelectric element is used to control the temperature of the capillary tubes within a predetermined range. It should be evident to one skilled in the art that the thermoelectric element 42 may be comprised of two or more individual elements. It should also be evident that alternate temperature control means such as circulating fluid systems, and air convection may also be used to control the temperature.

The capillary tubes 32 are arranged parallel to one another, side by side, in the window region 46. The length of each capillary tube from its first capillary end to the window region 46 is substantially the same for all the capillary tubes 32. This length is determined by the optimization of (i.e., minimum acceptable) sample run time, and the minimum acceptable resolution of the separated samples. Nominally, this length in on the order of 50–70 cm. The window region 46 represents the region allowing access to the parallel capillary tubes from incoming excitation light. It also allows access to outgoing fluorescence emission from the capillary tubes. Thus, the window region 46 allows the bands 50 in the various capillary tubes to be detected.

As shown in FIG. 1, an excitation light source comprising a laser 52 and a prism 54 is used to focus a light beam 56 through the window region 46 and onto the capillary tubes 32. A fluoresced light beam 58 is then sensed by a CCD camera 60, which captures the bands 50. As is known to those skilled in the art, other illumination and detection means can also be used.

The arrangement of FIG. 1 provides for the substantially simultaneous introduction of samples into the array of first capillary ends 38 of all the capillary tubes 32. In particular, the arrangement allows one to introduce the various samples by simultaneously dipping the array of first capillary ends 38 into the wells 62 of a sample-side microtitre tray 64 having a standard size, as described above.

To allow for this, the individual capillary ends are spaced apart from one another such that they have a spatial arrangement which is substantially the same as, that of an array of wells belonging to a microtitre tray of standard size. Thus, the spacing between adjacent first capillary ends is approximately 0.9 cm and the entire array of first capillary ends has a footprint less than 7.5 cm×11 cm, thus corresponding to a microtitre tray of standard size.

The array of second capillary ends 40 is inserted into the wells 66 of a second microtitre tray 68, where they come into contact with a buffer solution 70, as known to those skilled in the art. As the wells 66 in the second tray 68 are separated from one another, the chance of cross-contamination among the second capillary ends 40 is reduced.

A voltage source 72 is used to provide a voltage differential between the two arrays of capillary ends. As shown in FIG. 1, one voltage level is applied through individual leads 74 to each of the wells 62 of the first microtitre tray 64 and a second voltage level is applied in substantially the same manner through leads 76 to the wells 66 of the second tray 68. Thus, current flows through the leads 74, into the individual samples, through the first capillary ends 38, through the capillary tubes 32, through the second capillary ends 40, into the buffer 70 present in the wells 66 of the second microtitre tray 68, and finally through leads 76.

FIGS. 2A and 2B shows a top and a side view of one embodiment of a cartridge 80 in accordance with the present invention. The cartridge has a base member 82 formed from polycarbonate, acrylic or the like. Mounted in the base member are first and second mounting plates 84, 86, respectively. Preferably, these plates are formed from an electrically insulative material.

An array of first capillary ends 88 project from the bottom surface 90 of the first mounting plate 84 and an array of second capillary ends 92 project from the bottom surface 94 of the second mounting plate. The capillary tubes 96 pass through, and are retained in, plate holes formed in the plates 84, 86 and project from the top surfaces 98, 100 of the plates. Preferably, each of the capillary tubes 96 is protected by a tube assembly 102 which is secured to a plate hole in the mounting plate, as it passes through the mounting plates.

As best seen in FIG. 2A, the tube assemblies, each with its associated capillary tubes, form a rectangular array of 8 rows and 12 columns as they emerge from the plates 84, 86. The spacing between adjacent plate holes in which the assemblies 102 are held, and the spacing of adjacent capillary ends 88, 92 correspond to the spacing of adjacent wells in a microtitre tray of standard size. In the preferred embodiment, adjacent capillary ends are separated by approximately 0.9 cm and the entire array of capillary ends, and thus the array of plate holes through which the capillary tubes 96 pass, form a footprint no larger than about 7.5 cm×11.0 cm.

The upper surface 98, 100 of each mounting plate 84, 86 is provided with first and second enclosures designated by reference numerals 104, 106, respectively. In the preferred embodiment, each of the enclosures is provided with an inlet 108 and an outlet 110. The outlet 110 of the first enclosure is connected to the inlet 108 of the second enclosure by plastic tubing 112. The inlet 108 of the first enclosure is connected to a first plastic shut off valve 114 while the outlet 110 of the second enclosure is connected to a second plastic shut off valve 116. The plastic shut off valves 114, 116 are connected, in turn, to respective first and second quick disconnects 118, 120.

During operation, the cartridge 80 can be connected to a pump assembly 122 which is arranged to circulate a temperature-controlled liquid coolant through the enclosures 104, 106. In such case, the cartridge's first disconnect 118 is connected to the output 124 of the pump assembly 122 while the second disconnect 120 is connected to the input 126 of the pump assembly 122. Such an arrangement maintains the temperature of those portions of the capillary tubes 96 projecting from the upper surfaces 98, 100 of the mounting plates and present in the enclosures 104, 106. For this to work, the mounting plates 84, 86 must form a liquid-tight seal with the base member 82. A liquid-tight seal must also be formed between the plate holes and the tube assemblies 102 and/or the capillary tubes 96 themselves.

The capillary tubes 96 pass between the two arrays of tube assemblies 102 in an area of the cartridge not covered by the enclosures 104, 106. As explained above, thermoelectric temperature control means 128, or the equivalent, is arranged on either side of a window region 130 of the capillary tubes 96 to control the temperature of the capillary tubes when they are no longer within the enclosures 104, 106.

Within at least a portion of the window region 130, the capillaries 96 are arranged parallel to one another so that they may be read by detection means. Preferably, the base member 82 is provided with an opening 132 above which the window region 130 is situated. This allows for at least one of illumination means or detection means to be placed below the base member from where they may be in a direct line of sight to the exposed capillary tubes 96.

Figure 3A:
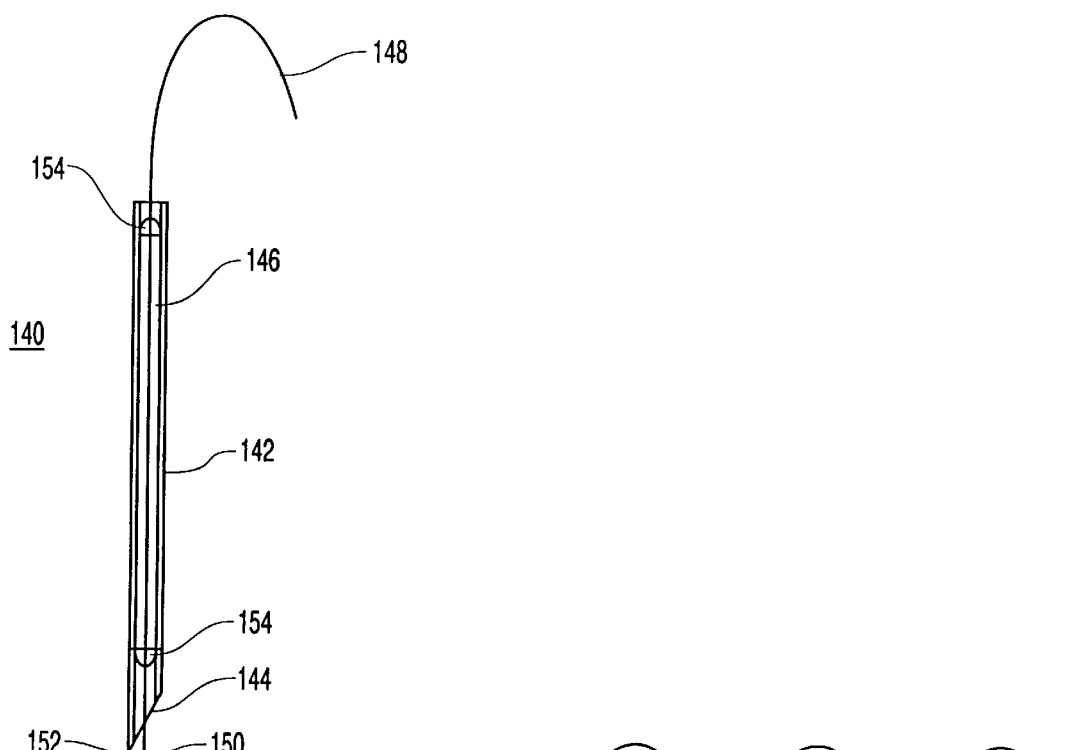
FIGS. 3A and 3B show a tube assembly and mounting arrangement for a cartridge of the present invention.
Figure 3B:
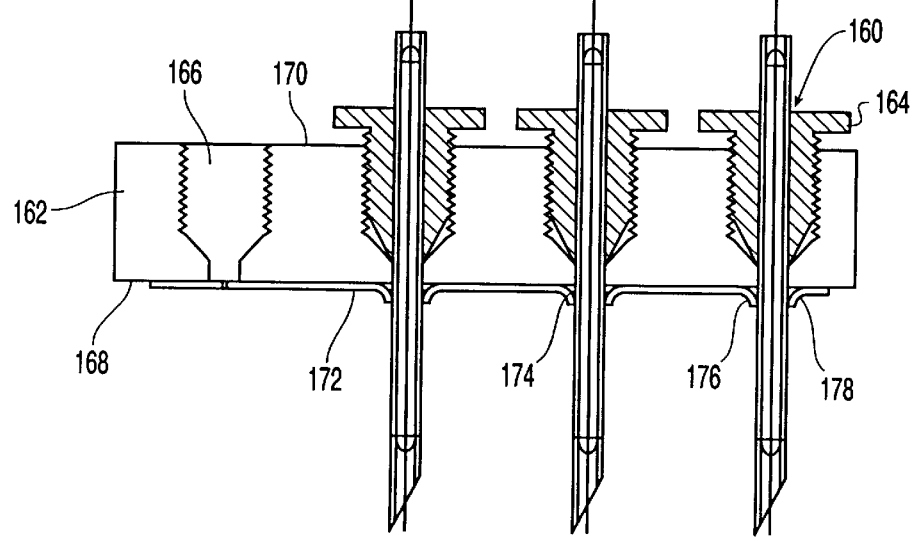

FIG. 3A shows a needle 140 used in forming a tube assembly 160 which can then be directly inserted into a mounting plate 162, as shown in FIG. 3B. The needle 140 comprises a metallic cannula 142. In the preferred embodiment, the cannula 142 is formed from stainless steel having an inner diameter of 0.064 in. and an outer diameter of 0.072 in. The cannula 142 is provided with a bevel 144 at the end which is dipped into a well.

Within the cannula 142 is a coaxially arranged annular polyetheretherketone (PEEK) polymer tubing 146 which serves as a sleeve. The polymer tubing 146 has an inner diameter of about 0.006 in. and an outer diameter of 0.0625 in. Thus, the polymer tubing 146 can be comfortably inserted into cannula 142.

Running through the center of the tubing 146, along a longitudinal axis of the needle 140, is a capillary tube 148 which is associated with the needle 140. The capillary tube 148 is formed from fused silica and has an inner diameter of about 0.003 in. and an outer diameter of about 0.006 in. Thus, the capillary tube 148 fits snugly into the polymer tubing 146. The capillary tube 148 terminates in an end 150 which is substantially across from the end 152 of the cannula 142. Thus, the spacing between the two ends 150, 152 is about 0.035 in.

An UV-cured, medical-grade epoxy sealant 154 is used at both ends of the polymer tubing 146 to secure it and the capillary tube 148 to the cannula 142. Preferably, the epoxy sealant 154 forms an air- and liquid-tight seal through the cannula 142. The epoxy sealant ensures that the polymer tubing 146 is not exposed to the environment, and also ensures that the capillary tube 148 does not come into direct contact with the cannula 142.

It should be noted that a needle may be formed in ways other than the one depicted in FIG. 3A. For instance, instead of a tubular cannula, the needle may simply comprise a capillary tube encased in a poured or coextruded plastic material which, in turn, is secured to a metallic strip. Other arrangements are also possible.

FIG. 3B shows a hollow, high pressure compression fitting 164 formed from nylon into which the needle 140 is inserted to complete the tube assembly 160. The needle 140 can be secured to the cylindrical inner walls of the compression fitting with an epoxy sealant. Each tube assembly 160 is then inserted into a plate hole 166 tapped in the mounting plate 162 and the plate hole 116, too, can be sealed with epoxy. When this is done, an air- and liquid-tight seal is provided between the bottom surface 168 and the top surface 170 of the mounting plate 162, allowing the mounting plate to withstand a positive pressure applied on its bottom surface in a region where the plate holes securing the tube assemblies are situated.

One may completely do away with the compression fittings 164 and drill plate holes in the mounting plate 162 which correspond in size to the outer diameter of the needles 140. In such case, a needle is directly inserted into each plate hole in the mounting plate 140 and secured thereto by the epoxy. Such a fitting-less approach can improve the structural integrity of the mounting plate 162 due to the reduced size of the plate holes. It may also provide a better air- and liquid-tight seal since there are fewer interfaces in which epoxy sealant is used. Moreover, it should also be understood that one may retain just a capillary tube 148, or just a capillary tube 148 encased in polymer tubing 146 directly in a plate hole of appropriate size formed in the mounting plate 162.

Whether or not one uses a compression fitting, and whether or not one uses a cannula and/or polymer tubing, it should be understood that in the preferred embodiment, each plate hole has one capillary tube retained therein. The array of plate holes preferably has a spatial arrangement corresponding to that of the wells of a microtitre tray of standard size. However, it may be possible to form the plate holes off-center, and then angle the capillary ends.

Furthermore, it should also be understood that it may be possible to fix an array of capillary ends in the desired configuration without forming holes in a mounting plate 162. For instance, this can be done by gluing or clamping the individual capillaries to a mounting plate so that their ends are arranged in the desired configuration. Alternatively, the capillaries may be secured together so that their ends remain in the desired configuration in a poured acrylic or the like. What is important is that the spacing of the capillary ends in the array correspond to the spacing of the wells in the microtitre tray of standard size.

A conductive plate 172 may be secured to the mounting plate 162 by screws, adhesives, or other conventional means. The conductive plate 172 is formed with an array of conductive holes 174 which corresponds to the plate holes 166 in the mounting plate. Each of the conductive holes 174 is formed by an H-shaped slit which forms a pair of tabs 176, 178 between the legs of the "H". When a needle 140 is inserted in the conductive hole 174, the tabs 176, 178 give way, and contact either side of the needle 140.

As the entire plate 172 is conductive, all needles 140 in the array share a common electrical connection. A voltage applied to the conductive plate 172 then appears on the exterior of each needle 140 in the array. During electrophoretic application, this voltage appears in the buffer solution found in each well, into which solution the capillary end 150 is inserted.

As is known to those skilled in the art, the voltage differential may be delivered to the first capillary ends through other means as well. For instance, instead of contacting a common plate to which the needles are connected, voltage leads may be connected directly to each needle. Alternatively, individual leads may be dipped into the liquid in each well. Another alternative is to deliver the voltage through a metallic coating, such as gold, deposited on the exterior of only the terminal portion of each capillary tube, where it contacts the liquid in the well. Also, the voltage may be delivered directly to the wells through one or more leads, as described earlier. One skilled in the art can readily formulate alternative approaches to delivering a voltage to the first capillary end.

Figure 4:
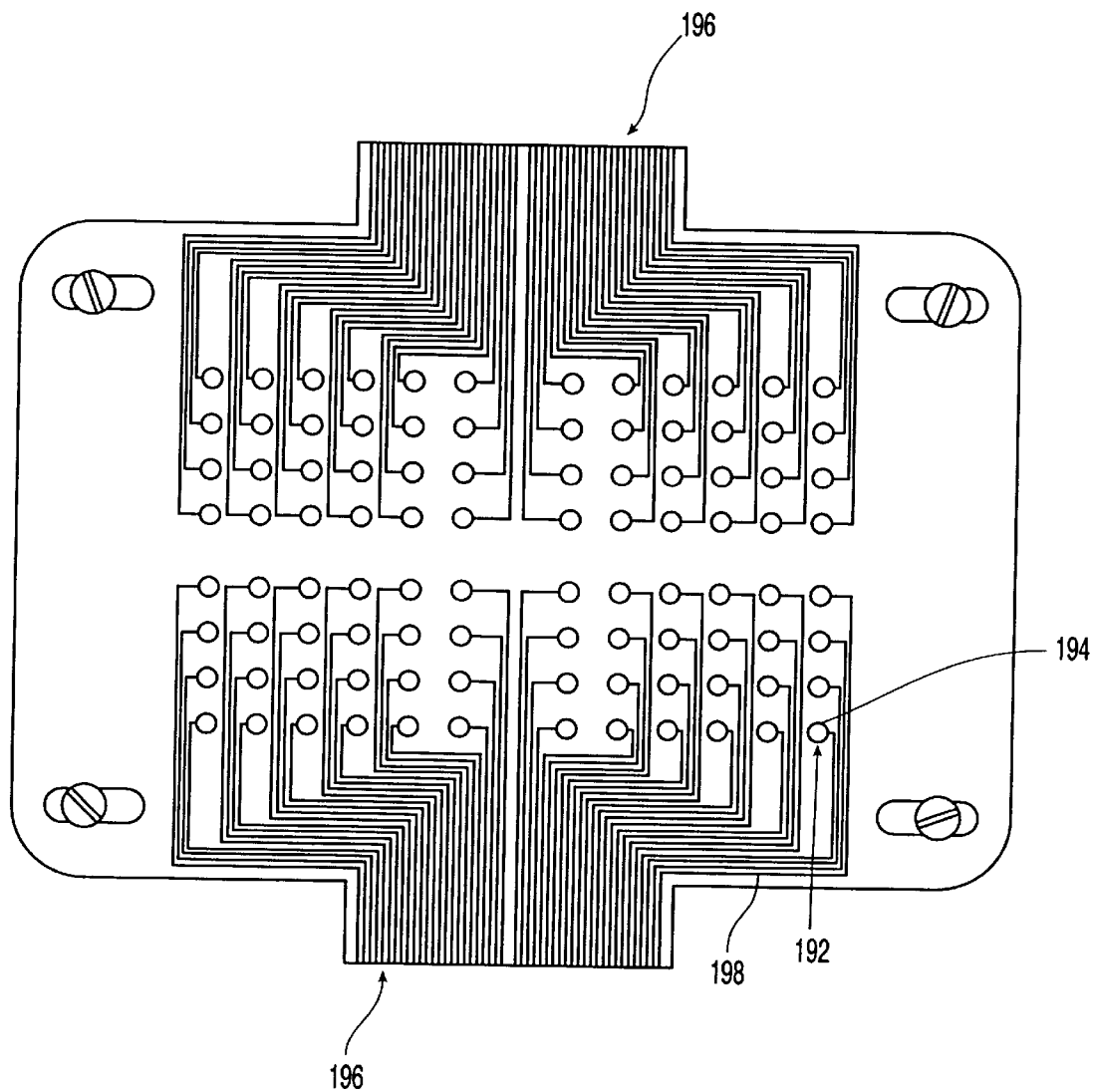
FIG. 4 shows a monitor plate which can be used with an array of needles.

FIG. 4 shows a monitor plate 190 which can be used with the cartridge embodiment shown in FIGS. 2A and 2B. In a cartridge of the present invention, the needles of at least the first mounting plate 84 are provided with a conductive plate 172 described above. The needles of the second mounting plate 86 can be provided with a monitor plate 190.

The monitor plate has an array of monitor holes 192. The array of monitor holes is aligned with the second array of plate holes formed in the second mounting plate 86. Each monitor hole 192 is formed with an isolated electrical contact 194 which is electrically connected to a monitor plate connector 196 by an individual lead 198. Each needle in the second mounting plate 86 contacts a corresponding electrical contact 194 in the monitor plate.

The purpose of the monitor plate is to provide a means for gauging the presence of electrical conductivity between any needle in the second mounting plate 86 and the needles of the first mounting plate 84. In this regard, it should be understood that the monitor plate 190 can be secured to mounting plate 86 in much the same manner as the conductive plate 172. What is important is that each of the electrical contacts 194 connects to only one needle in the second mounting plate.

Figure 5:
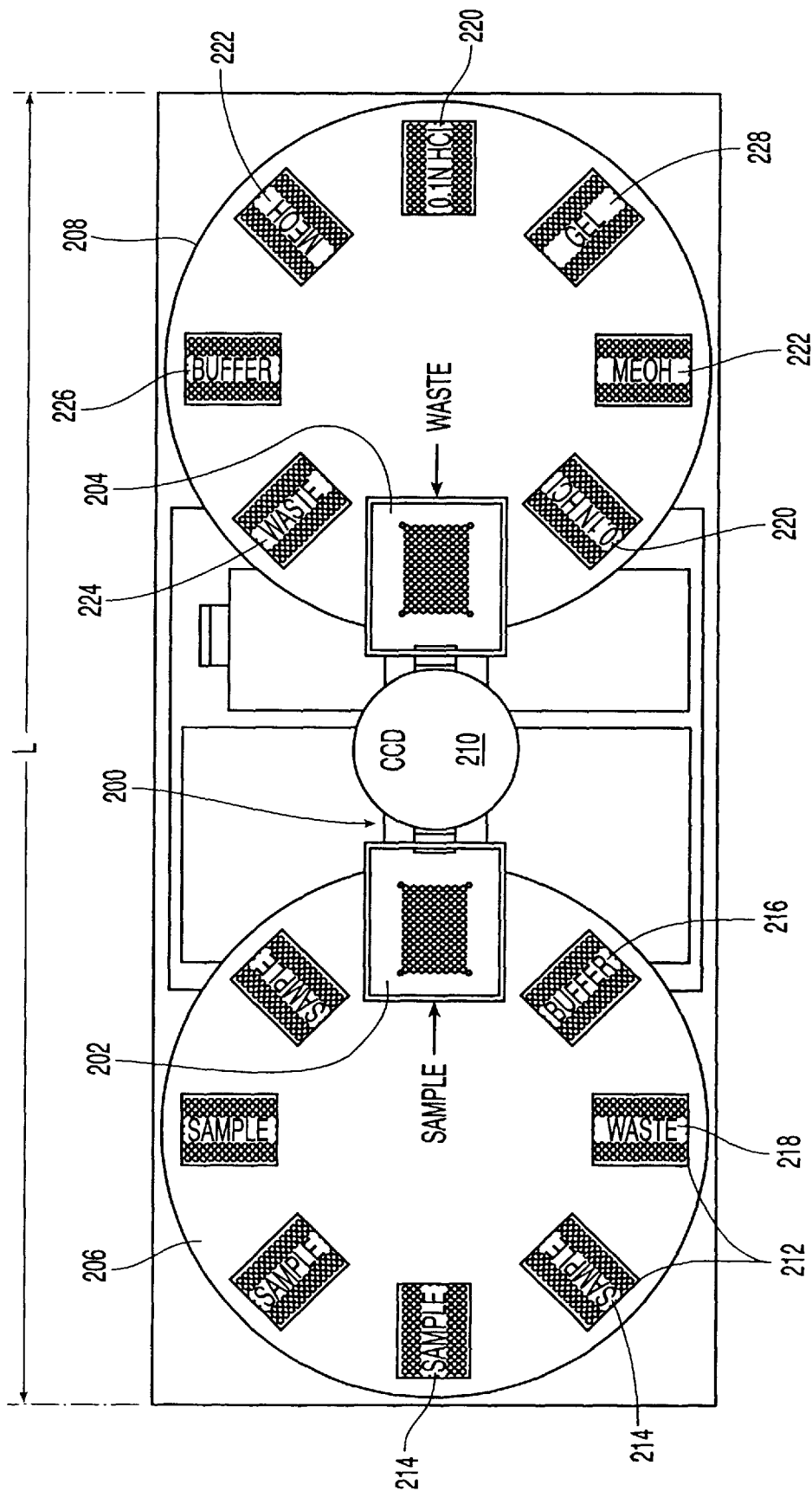
FIG. 5 shows the arrangement of an apparatus which can be used with the cartridge of FIGS. 2A & 2B.

FIG. 5 shows a cartridge 200 having a first 202 and a second 204 array of needles arranged above a first 206 and a second 208 carousel, each array positioned above a portion of a respective carousel. A CCD camera 210 is positioned above a portion of the cartridge between the two to detect bands in the capillary tubes (not shown in FIG. 5). Each carousel 206, 208, has eight platforms 212, on each of which a microtitre tray having a standard size is placed.

The wells in each of these trays hold one or more liquids such as samples, gels, buffer solutions, acidic solutions, basic solutions, etc. As configured in FIG. 5, the first carousel holds 6 sample trays 214, 1 buffer tray and 1 waste tray, a sample tray being positioned underneath the first needle array 202. As also shown in FIG. 5, the second carousel holds a pair of acidic solution trays 220, a pair of basic solution trays 222, a pair of waste trays 224, one of which is positioned underneath the second needle array 204, a buffer solution tray 226, and a gel tray 228. Thus, the first carousel 206 is the sample-side carousel and the second carousel 208 is the gel-side carousel.

The cartridge is removably mounted to an automated electrophoretic apparatus. During operation, a lifting means raises and lowers the platform 212 which is under either of the two needle arrays 202, 204. When a microtitre tray is brought in close proximity to one of the needle arrays 202, 204, the needles in these arrays, and their associated capillary ends, are dipped into the contents of each well of that microtitre tray. When the platform under either of the needle arrays is lowered, the carousel associated with that platform may be rotated so that a different platform 212 holding a different microtitre tray, can be raised.

When a platform is raised, surfaces around the periphery of the platform abut opposing surfaces, thus sealing a pressure chamber beneath the bottom surface of the needle array. Introducing a pressurized inert gas, such as helium, into the chamber at a pressure of 30 psi or so, applies a uniform force to the samples in the wells of the microtitre tray held on that platform. This causes a portion of each of samples to enter into the corresponding array of first capillary ends.

With, or in place of, applying pressurized helium to introduce samples into the first capillary ends, one may also apply a high voltage for brief period of time, on the order of 20–40 seconds, to cause the samples to migrate into the first capillary ends. Using a high voltage for this purpose, however, may be size-selective. That is, smaller molecules are more likely to enter the first capillary ends, potentially distorting the subsequent electrophoresis analysis.

The operation of the automated electrophoretic apparatus in accordance with FIG. 5 will now be described. First, the various microtitre trays are loaded with the designated buffer solutions, gels, samples, etc. Then, gel tray 228 in carousel 208 is raised and gel is introduced into the capillary tubes (not shown in FIG. 5) through second capillary ends (hidden in FIG. 5) associated with the second needle array 204. The gel tray 228 is then lowered. A sample tray 214 in carousel 206 is then raised, and sample is introduced through the first capillary ends (hidden in FIG. 5) associated with the first needle array 202. The sample tray 214 is then lowered. Carousels 206 and 208 are then rotated to position buffer trays 216 and 226 under their respective needle arrays 202 and 204. A voltage differential is then applied across the two needle arrays to perform the electrophoresis run.

Upon completion of the run, the cartridge may be reconditioned. This is done by flushing out the gel and samples from the previous run under pressure and cleaning the capillary tubes using the acidic 220 and/or basic 222 solutions. The cartridge is then ready for re-use, allowing the samples in another one of the sample trays 214 to be tested.

It should be obvious that the carousels 204, 206 may be formed with a different number of platforms. It should also be obvious that one can use a linear, or rectangular, or other arrangement of such platforms. All that is required is a storage and positioning system which allows a first particular microtitre tray to be brought to the first needle array 206, and a second particular microtitre tray to be brought under the second needle array 208.

FIGS. 6A and 6B present a side and a top view, respectively, of a cartridge 280 having a first mounting plate 282 in which the array of plate holes in the first mounting plate 282 is rotated by 90°. Otherwise, the arrangement for connecting the capillary tubes to the first mounting plate is substantially the same as previously described. The first capillary ends formed in an array with the desired spacing project from the bottom surface of the first mounting plate 282, and are retained in plate holes formed in the first mounting plate.

The second mounting plate 284, however, is not the same as in the previous cartridge embodiment. In the cartridge 280, the second mounting plate 282 serves as a pressure containment member of a pressure cell 286 having substantially cylindrical exterior walls. For the sake of clarity, FIG. 6A does not show all the capillary tubes on the first mounting plate, nor any capillary tubes at all on the second mounting plate 284. It is to be understood, however, that all the capillary tubes are present.

The second mounting plate has a radially symmetric, beveled surface 288 in which a plurality of plate holes 290 are formed. Each of these plate holes 290 is fitted with a section of PEEK polymer tubing 292 in which the capillaries are encased using an UV-cured epoxy, as described before, to form an air- and liquid-tight seal in the plate holes 290. The capillary tubes pass through the PEEK polymer tubing and a second end of each capillary tube communicates with an interior cavity of the pressure cell. Although the preferred embodiment for this cartridge uses just PEEK polymer tubing and a capillary tube in the second mounting plate, it should be understood, that needles similar to the ones described earlier, could also be used. Also, just the capillary tubes alone, secured by epoxy, can be used as well. What is important is that each capillary tube 294 is retained in a plate hole 290 in an air- and liquid-tight manner, and that the capillary tube's second end communicates with an interior cavity of the pressure cell 286.

As is the case with cartridge 80 of FIGS. 2A and 2B, this cartridge 280 is provided with thermoelectric control means 298, enclosures 300, 302, and its capillary tubes are arranged in parallel along at least a portion of a window region 304. Although not shown in FIGS. 6A and 6B, it is understood that the enclosures 300, 302 can be provided with inlets and outlets and the like for circulating a coolant, as was the case with the other cartridge 80.

As shown in FIG. 6A, the second mounting plate 284 has a truncated cone-shaped upper portion terminating in a flat top 310. The curved, conical surface 288 in which the plate holes 290 are formed, is advantageous for reasons of structural integrity when a high positive pressure is applied from underneath the second mounting plate. Also, placing the plate holes 290 on such a surface allows them to be placed farther apart, a feature which also enhances the structural integrity of the pressure cell 286.

The pressure cell 286 is secured to the base member of the cartridge 280 and projects through the bottom of the base member. This arrangement allows the pressure cell 286 to be provided with an inlet 312 and an outlet 314 arranged on opposite sides of its cylindrical exterior walls. It should be noted that the inlet could just as easily be formed in the flat top portion 310 of the second plate 284, and the outlet formed in the bottom surface of a lower portion 316 of the pressure cell 286. In such case, the pressure cell could rest on the base member, rather than project through its bottom, with a pipe fitting connected to the outlet through a hole formed in the base member, which hole is then sealed.

Figure 7:
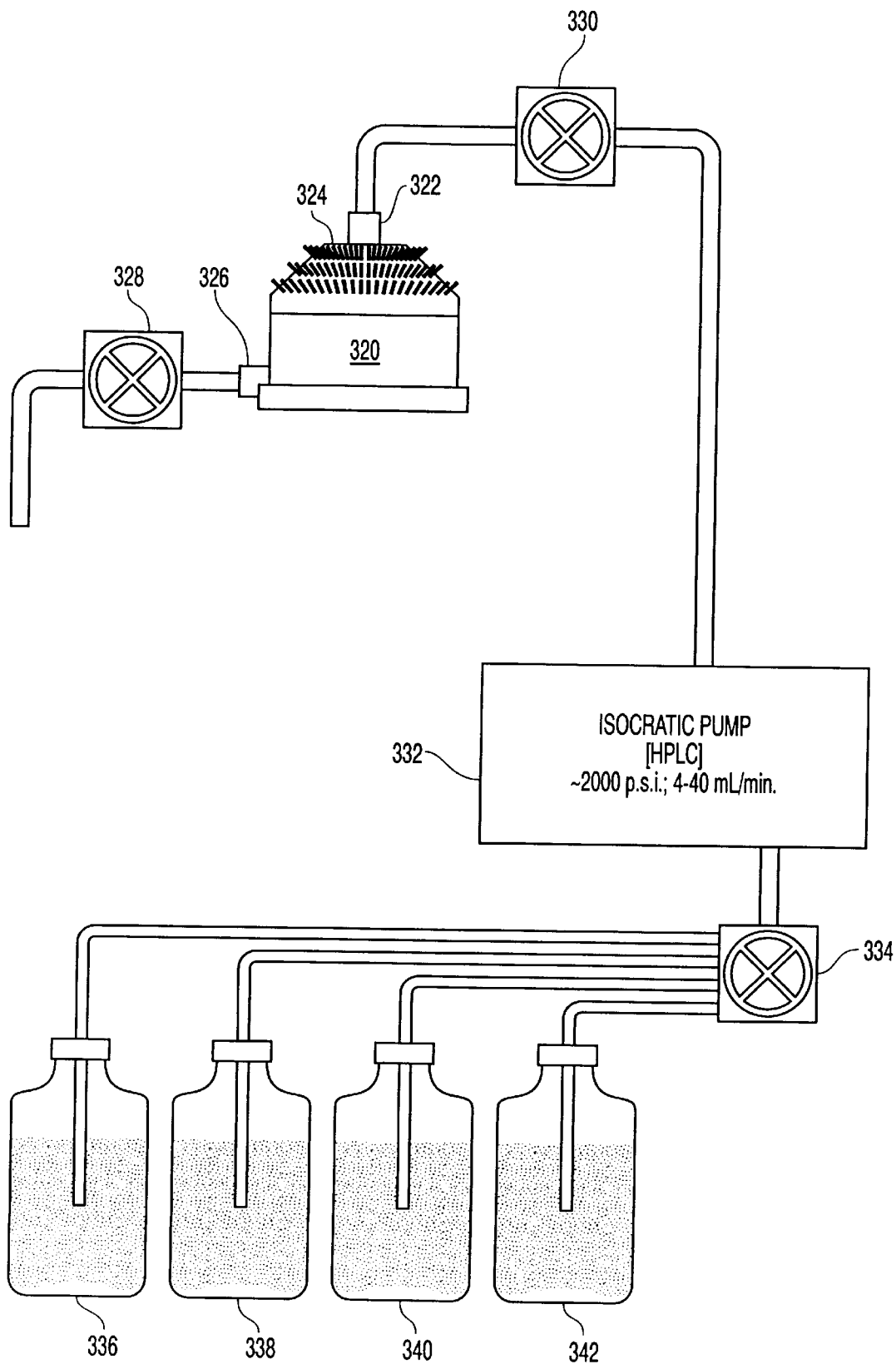
FIG. 7 shows the valving arrangement for a pressure cell similar to the one shown in the cartridge of FIGS. 6A and 6B.

FIG. 7 shows a valving arrangement for a pressure cell 320 which has an inlet 322 at its top surface 324, but otherwise is substantially similar to the pressure cell 286. Aside from the inlet 322, the pressure cell 320 is also provided with an outlet 326, which is connected to a waste valve 328. The waste valve 328 is opened to expel the contents of an interior cavity of the pressure cell 320.

Access to the inlet is 322 controlled by a shut-off valve 330. Liquids can be passed through the inlet 322 into the pressure cell 320 with the use of a pump 332. Preferably, the pump is a high pressure liquid chromatography (HPLC) pump having a pumping capacity of 4–40 milliliters per minute, at a pressure of about 2000 psi. The pump 332 is connected to a multi-valve manifold 334 which selectively allows one of four liquids to be pumped into the pressure cell. The four liquids are held in separate containers 336, 338, 340, 342, which respectively hold gel, a buffer solution, an acidic solution, and a basic solution. Additional containers holding the same liquids may be held in reserve, or connected in series with these, so as to increase the total supply.

The waste valve 328, the shut-off valve 330, the pump 332 and the multi-valve manifold 334 are all under the direction of a controller, preferably a microcomputer, or equivalent. Thus, the contents of an interior cavity of the pressure cell are regulated by the controller. Such a controller may also receive inputs from various pressure and temperature monitors and other sensors to prevent damage to the pressure cell 320.

During operation, the interior cavity of the pressure cell 320 is filled by means of the pump 332. This forces the pumped liquid into the second capillary ends which communicate with the interior cavity of the pressure cell 320. By filling the array of first capillary ends and the pressure cell 320 with the appropriate fluids in the appropriate sequence, one may perform the electrophoresis operations, much as described above with regard to the apparatus of FIG. 5.

After the run, one may recondition the pressure cell and the capillary tubes to prepare them for another run. Again, this is accomplished by flushing the gel and sample from all the capillary tubes simultaneously. With the pressure cell 320, however, pressures on the order of several thousand psi can be applied. These increased pressures force the viscous gel out of the capillary tubes much faster. This reduces the cycle time between runs, with reconditioning, to about one to two hours.

Figure 8:
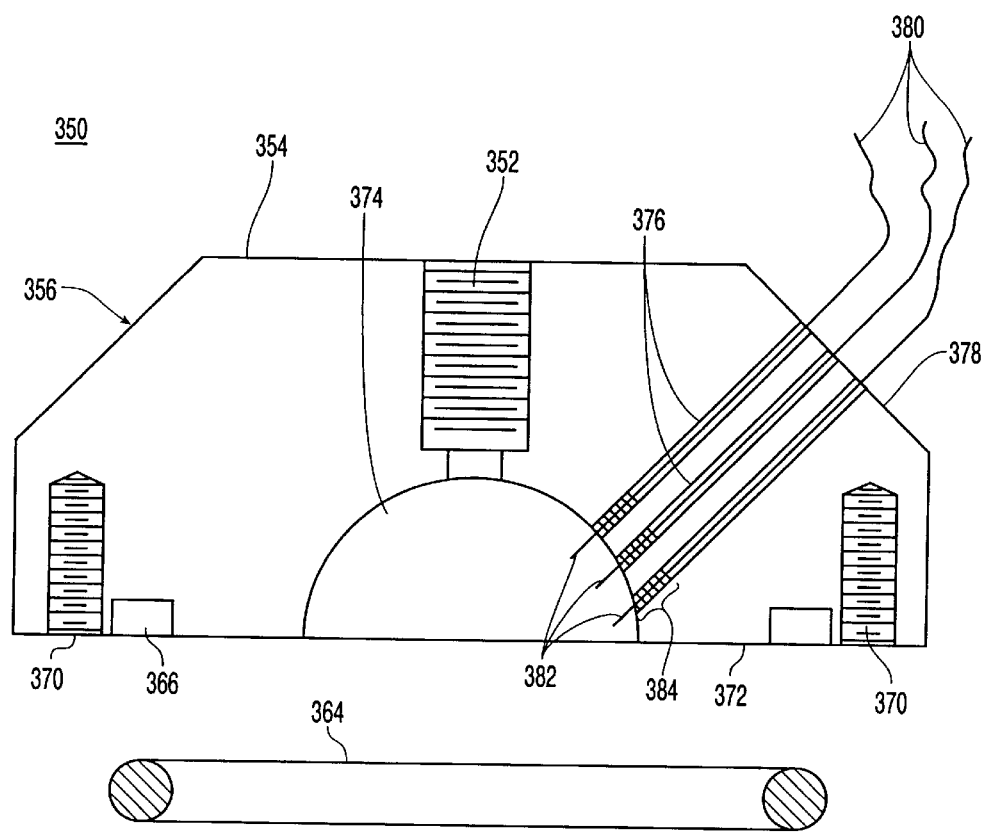
FIG. 8 shows an exploded view of a pressure cell vertical cross-section.
Figure 8:
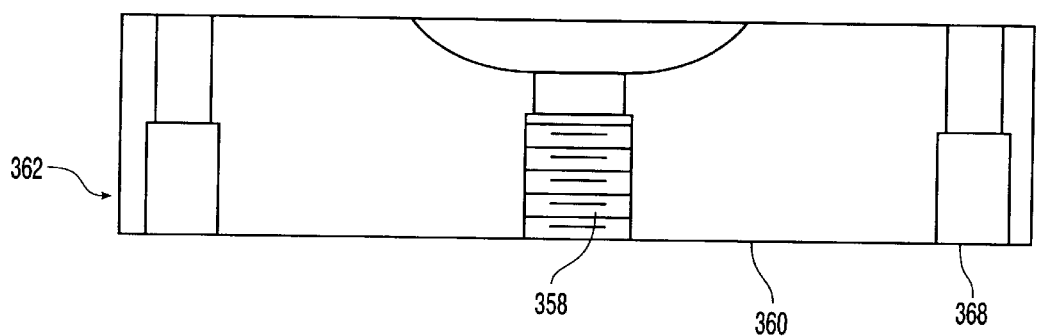

FIG. 8 shows an exploded cross-section of a pressure cell 350, similar to the pressure cell 286 in the cartridge 280. As is the case with the other pressure cells, pressure cell 350 is preferably formed from aluminum or stainless steel. The pressure cell 350 is provided with a threaded inlet 352 formed on the top surface 354 of its upper portion 356, which upper portion comprises the second mounting plate. The pressure cell 350 is also provided with a threaded outlet 358 on the bottom surface 360 of its lower portion 362. High pressure pipe fittings can be screwed into the threads of the inlet 352 and the outlet 358.

The upper portion 356 and the lower portion 362 are held together by a plurality of bolts (not shown) which are inserted through bolt holes 368 formed along the periphery of the bottom surface 360 of the lower portion 362. The bolts are then screwed into corresponding threaded holes 370 formed on the bottom surface 372 of the upper portion 356. An O-ring 364 partially fits into a rectangular channel 366 formed in the second mounting plate 356. The O-ring 364 provides a seal between the upper portion 356 and the lower portion 362. Instead of an O-ring, a gasket, or the like may be used to effect such a seal.

At the center of the pressure cell 350, formed between the upper 356 and lower 362 portions is an interior cavity 374. A plurality of plate holes 376 are formed in the upper portion (second mounting plate). For simplicity, in FIG. 8, the plate holes 376 are only shown on one side of the upper portion 356. It should be understood, however, that they are also present on the other side. The plate holes 376 extend from a beveled surface 378 formed on the upper portion 356 to the interior cavity 374.

Capillary tubes 380 are retained in these plate holes 376 and their second ends 382 communicate with the interior cavity 374. Preferably, each capillary is encased in a section of PEEK polymer tubing which extends from a point within each plate hole 376, proximate to the interior cavity 374, to well outside the beveled surface 378. For simplicity, however, the PEEK tubing is not shown in FIG. 8. Nevertheless, it should be kept in mind that just the capillary tube, or a needle comprising a capillary tube, PEEK tubing and a cannula, can be inserted into each plate hole 376, assuming that it is suitably sized.

As explained above, an UV-cured epoxy sealant is used to seal the plate holes 376 at both ends so that they are air- and liquid-tight. With the pressure cell, the terminal portion 384 of each plate hole proximate to the interior cavity 374 is tapped or roughened. This provides a surface to which the epoxy sealant bonds more readily during assembly.

A liquid held within the interior cavity 374 is in contact with the material forming the interior cavity. When the liquid is also in contact with the second capillary end 382, an electrical connection between the interior cavity 374 of the pressure cell 350 and the first capillary end secured to the first mounting plate, is completed. Thus, grounding the pressure cell 350 through a contact formed thereon, applies the ground to the interior cavity 374, completing the circuit necessary to perform the electrophoresis. Alternatively, as the pressure cell 350 is electrically isolated from the base member to which it is mounted, the potential of the pressure cell 350 may be allowed to float. This allows one to apply a high voltage to the pressure cell 350, rather than to the needles associated with the first capillary ends.

Figure 9:
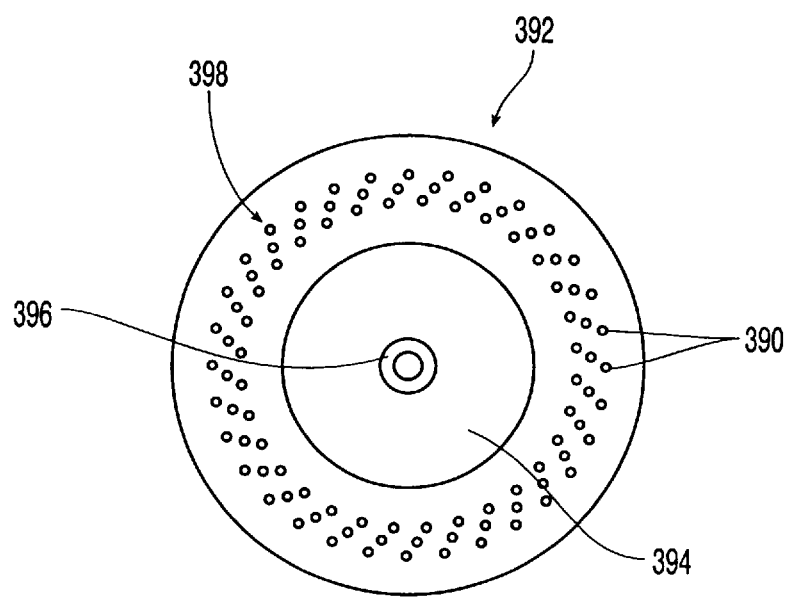
FIG. 9 shows a top view of a second mounting plate of a pressure cell having an alternate arrangement of plate holes.

FIG. 9 shows an alternate arrangement for the plate holes 390 in a second mounting plate 392 having a top surface 394 and an inlet 396. In this arrangement, each set 398 of three plate holes is offset at an angle relative to the center of the top surface 394. This provides for a maximum spacing between the plate holes. From a structural integrity point of view, such an arrangement may be preferable to having the plate holes arranged radially, in a spoke-like fashion, as shown in FIG. 6B.

Figure 10:
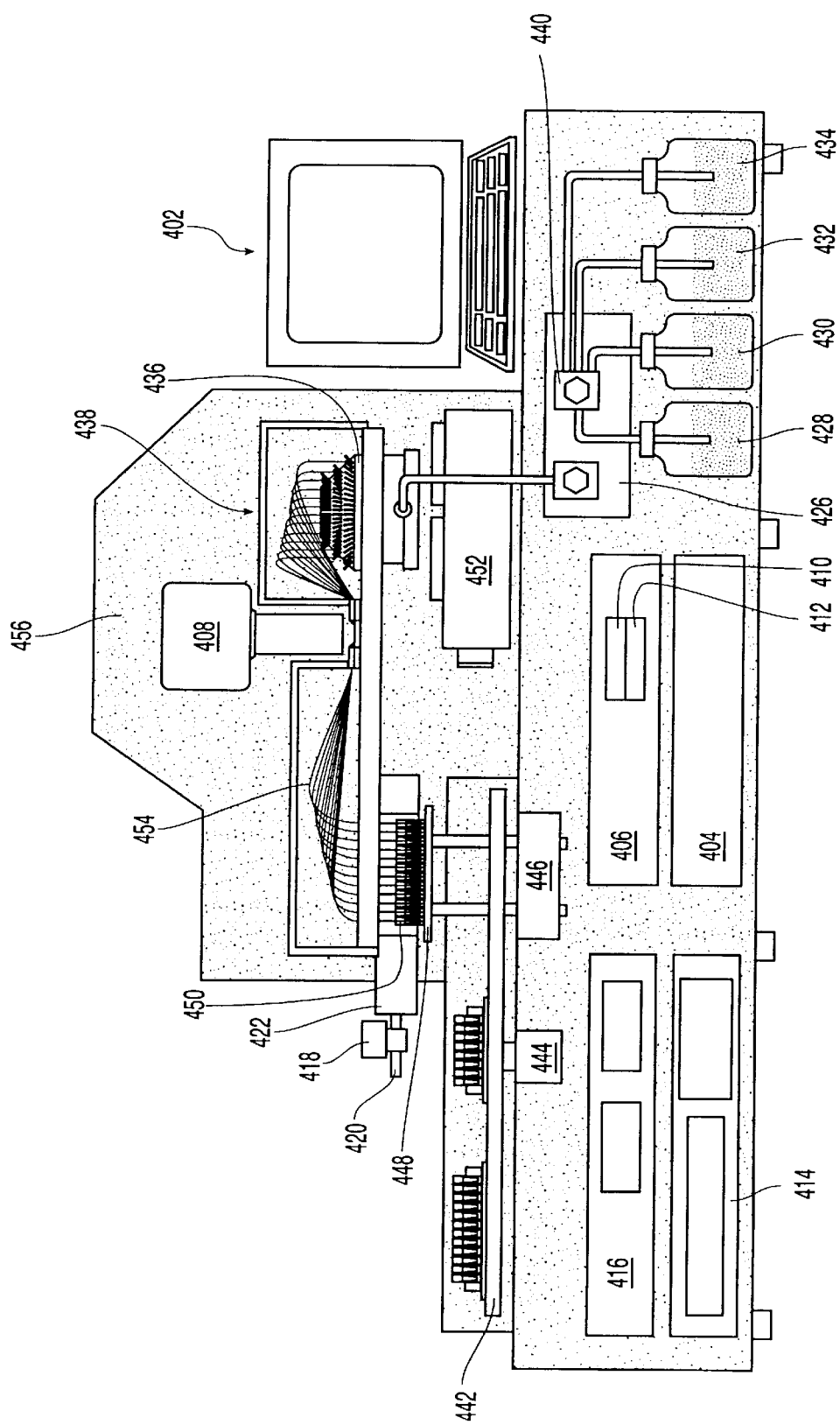
FIG. 10 shows an electrophoretic apparatus in accordance with the present invention.

FIG. 10 shows an electrophoretic apparatus 400 designed for use with a capillary cartridge formed in accordance with FIGS. 6–9. The apparatus comprises a user interface 402, shown as a video display terminal and keyboard, which communicates with a controller 404, which preferably is a microprocessor-based computer, or the like. The user interface 402 allows a user to enter commands, receive status information, and view the collected data.

The apparatus 400 also comprises a data processing computer 406, which receives, stores and processes video signals from a CCD camera 408. The data processing computer 406 is provided with optical 410 and/or magnetic 412 read/write data storage means. Resident in the data processing computer 406 are signal and image processing software to analyze the signal data from the camera 400. The data processing computer 406 is connected to the controller 404, and responds to requests from the latter, exchanging data and control information, as needed.

The apparatus 400 is further provided with a high-voltage power supply 414 which provides the necessary voltage to be applied across the ends of the capillary tubes. The power supply's operation is directed by the controller 404.

The controller 404 also directs the operation of a pump interface 416, which comprises a number of electronic switches. The pump interface 416 regulates the operation of a solenoid valve 418. The solenoid valve 418 connects a gas inlet 420 which is connected to an inert gas source, such as a pressurized helium tank, to the chamber 422. The pump interface 416 also regulates the operation of high pressure liquid chromatography (HPLC) pump 426. The HPLC pump 426, under the direction of the controller, selectively supplies liquids in a gel container 428, a buffer solution container 430, an acid container 432, and a base container 434, to a pressure cell 436 of a cartridge 438 through a multivalve manifold 440.

A carousel 442 having a plurality of platforms 448 is turned by a rotor 444. A lifting means 446, such as a hydraulic pump or the like, raises and lowers a platform 448 positioned under a first mounting plate. This brings a microtitre tray 450 on the platform 448 towards and away from an array of capillary ends, as previously described. Both the rotor 444 and the lifting means are connected to, and driven by, the controller 404.

The apparatus 400 also includes a light source 452, preferably a laser, which illuminates the capillary tubes 454, as directed by the controller 404. The light source 452 illuminates the capillary tubes 454 from below, through an opening in a base member of the cartridge 438, as previously described. A light shroud 456 covers the camera 408, the light source 452, and at least the window region of the capillary tubes 454, as the detection of the capillary bands is performed in the dark.

During operation, the capillary tubes 454 are first cleaned and then loaded with gel through the pressure cell 436 by activating pump 452. The pump 452 is then turned off. Next, a platform 448 carrying a microtitre tray 450 holding samples is raised by the lifting means 446. This forms a seal between the platform 448 and the underside of the chamber 422. It also dips the first capillary ends into the wells of the microtitre tray 450. With the chamber 422 sealed, the solenoid valve 418 is opened, allowing pressurized helium gas to enter through the inlet 420. This puts a uniform positive pressure on the samples in each of wells of the microtitre tray 450, on the order of 30 psi, and forces the samples at least slightly into the first capillary ends. As discussed above, a high voltage may be applied for a brief period of time for this purpose, as well. The platform 448 is lowered and the carousel 442 is rotated, bringing a microtitre tray filled with buffer solution under the first capillary ends. Next, the buffer tray is raised so that the first capillary ends are dipped into the buffer solution, and the pressure cell 436 is filled with buffer solution so that the second capillary ends are in contact with buffer solution, as well. After this, the high voltage source 414 is turned on to perform the electrophoresis run. The light source 452 and the camera 408 are used to simultaneously detect the bands in all the capillary tubes 454. The video signal data from the camera 408 are processed and stored in the computer 406. The processed data may then be presented on the user interface 402. After the run, the cartridge 438 may be reconditioned (i.e., cleaned) and prepared for another run.

While the above invention has been described with reference to certain preferred embodiments, it should be kept in mind that the scope of the present invention is not limited to these. One skilled in the art may find variations of these preferred embodiments which, nevertheless, fall within the spirit of the present invention, whose scope is defined by the claims set forth below.

What is claimed is:

1. An apparatus for use in capillary electrophoresis comprising:
    a first mounting plate having a first side and a second side and having an array of plate holes formed therein; and
    a plurality of capillary tubes, each having first and second capillary ends, each capillary tube being retained in one of said plate holes proximate to its first capillary end, said first capillary end projecting on said first mounting plate first side, wherein
    centers of said projecting first capillary ends are spaced apart from one another, forming a two-dimensional array of first capillary ends, said array of first capillary ends having a spatial arrangement corresponding to that of an array of wells associated with a microtitre tray, and
    said capillary tubes are arranged parallel to one another at a window region thereof, a length from said first capillary ends to said window region being substantially the same for all capillary tubes.

2. The apparatus of claim 1, wherein
    said array of first capillary ends is rectangular, having 8 rows and 12 columns, and dimensions of less than 7.5 cm×11.0 cm; and
    a spacing between centers of adjacent first capillary ends in a row, and adjacent first capillary ends in a column, is approximately 0.9 cm.

3. The apparatus of claim 1, further comprising:
    an enclosure surrounding the first mounting plate second side, a portion of each of said capillary tubes being present in said enclosure.

4. The apparatus of claim 1, wherein the plate holes having the capillary tubes retained therein, are provided with a sealant to form an air-tight seal between the first side and the second side.

5. The apparatus of claim 4, further comprising:
    a plurality of needles having a common electrical connection, each needle being secured in one of said plate holes of said first mounting plate, each capillary tube associated with a needle.

6. The apparatus of claim 5, further comprising:
    a first conductive plate arranged to provide said common electrical connection, said first conductive plate having an array of contact holes aligned with said array of plate holes, each of said needles passing through a corresponding contact hole and contacting said first conductive plate.

7. The apparatus claim 6, wherein said array of plate holes is rectangular, having 8 rows and 12 columns, and dimensions of less than 7.5 cm×11.0 cm.

8. An apparatus for use in capillary electrophoresis in which samples are introduced into a plurality of capillary tubes from an array of wells of a microtitre tray, said apparatus comprising:
    spaced apart first and second mounting plates, each having a first and a second side, and each having an array of plate holes formed therein;
    a plurality of capillary tubes, each having first and second capillary ends, each capillary tube being retained proximate to its first capillary end in one of said plate holes on the first mounting plate and also being retained proximate to its second capillary end in a corresponding plate hole in the second mounting plate, said first capillary end projecting on said first mounting plate first side and said second capillary end projecting on said second mounting plate first side, wherein
    centers of said projecting first capillary ends are spaced apart from one another, forming a two-dimensional array of first capillary ends, said array of first capillary ends having a spatial arrangement corresponding to that of an array of wells associated with a first microtitre tray, and
    centers of said projecting second capillary ends are spaced apart from one another, forming an array of second capillary ends, said array of second capillary ends having a spatial arrangement corresponding to that of an array of wells associated with a second microtitre tray.

9. The apparatus of claim 8, wherein
    said arrays of first and second capillary ends are rectangular, having 8 rows and 12 columns, and dimensions of less than 7.5 cm×11.0 cm; and
    a spacing between centers of adjacent capillary ends in a row, and adjacent capillary ends in a column, is approximately 0.9 cm.

10. The apparatus of claim 8, further comprising:
    first temperature control means arranged on either side of a window region of said capillary tubes, said window region being situated between said first mounting plate and said second mounting plate, wherein
    said capillary tubes are arranged parallel to one another along at least a portion of said window region.

11. The apparatus of claim 10, wherein
    a length from said first capillary end to said window region, is substantially the same for all capillary tubes.

12. The apparatus of claim 8, further comprising
    a first enclosure around said first mounting plate second side and a second enclosure around said second mounting plate second side, at least a portion of the capillary tubes being present in each enclosure.

13. The apparatus of claim 12, further comprising:
    an inlet and an outlet formed in each enclosure; and
    tubing connecting the outlet of one enclosure with the inlet of the other enclosure.

14. The apparatus of claim 13, further comprising:
    first temperature control means arranged on either side of a window region of said capillary tubes, said window region being situated between said first and second enclosures, wherein
    said capillary tubes are arranged parallel to one another along at least a portion of said window region.

15. The apparatus of claim 8, wherein the plate holes having the capillary tubes retained therein, are provided with a sealant to form an air-tight seal between the first side and the second side of at least one mounting plate.

16. The apparatus of claim 15, further comprising:
   a first plurality of needles having a common electrical connection, each of said first plurality of needles being secured in one of said plate holes of said first mounting plate, a first end of each capillary tube being associated with one needle in said first mounting plate; and
   a second plurality of needles, each of said second plurality of needles being secured in one of said plate holes of said second mounting plate, a second end of each capillary tube being associated with a corresponding needle in said second mounting plate.

17. The apparatus of claim 16, further comprising:
   a first conductive plate arranged to provide said common electrical connection, said first conductive plate having an array of contact holes aligned with said array of plate holes of said first mounting plate, each of said needles passing through a corresponding contact hole and contacting said first conductive plate.

18. The apparatus of claim 17, further comprising:
   a monitor plate having an array of monitor holes aligned with said second array of plate holes, each monitor hole formed with an isolated electrical contact which is electrically connected to a monitor plate connector, and wherein
   each needle secured to a plate hole in said second mounting plate passes through a corresponding one of said monitor holes and is electrically connected to one of said isolated electrical contacts.

19. The apparatus of claim 18, wherein
   each of said array of plate holes is rectangular, having 8 rows and 12 columns, and dimensions of less than 7.5 cm×11.0 cm.

20. In which samples are introduced from an array of wells associated with a microtitre tray, said apparatus comprising:
   a first mounting plate having a first side, a second side and a first array of plate holes formed therein;
   a plurality of capillary tubes, each having first and second capillary ends, each capillary tube being retained in one of first array of said plate holes, proximate to its first capillary end, said first capillary end projecting on said first mounting plate first side, said centers of said projecting first capillary ends being spaced apart from one another, forming a two-dimensional array of first capillary ends, said array of first capillary ends having a spatial arrangement corresponding to that of an array of wells associated with a microtitre tray, and
   a pressure cell having an inlet, an outlet, an interior cavity, and a second mounting plate arranged as a pressure containment member of said pressure cell,
   said second mounting plate having a first side and a second side, and a plurality of plate holes formed therein, each capillary tube being retained in one of said plurality of plate holes of said second mounting plate and communicating with said interior cavity.

21. The apparatus of claim 20, wherein
   said array of first capillary ends is rectangular, having 8 rows and 12 columns, and dimensions of less than 7.5 cm×11.0 cm; and
   a spacing between centers of adjacent first capillary ends in a row, and adjacent first capillary ends in a column, is approximately 0.9 cm.

22. The apparatus of claim 20, wherein the plate holes on the second mounting plate are formed on a radially symmetric curved surface thereof.

23. The apparatus of claim 20, further comprising:
   first temperature control means arranged on either side of a window region of said capillary tubes, said window region being situated between said first mounting plate and said second mounting plate, wherein
   said capillary tubes are arranged parallel to one another along at least a portion of said window region.

24. The apparatus of claim 20, wherein
   a length from said first capillary end to said window region, is substantially the same
   for all capillary tubes.

25. The apparatus of claim 20, further comprising
   a first enclosure around said first mounting plate second side and a second enclosure around said second mounting plate second side, at least a portion of the capillary tubes being present in each enclosure.

26. The apparatus of claim 25, further comprising:
   an inlet and an outlet formed in each enclosure; and
   tubing connecting the outlet of one enclosure with the inlet of the other enclosure.

27. The apparatus of claim 26, further comprising:
   first temperature control means arranged on either side of a window region of said capillary tubes, said window region being situated between said first and second enclosures, wherein
   said capillary tubes are arranged parallel to one another along at least a portion of said window region.

28. The apparatus of claim 20, wherein the plate holes having the capillary tubes retained therein, are provided with a sealant to form an air-tight seal between the first side and the second side of at least one mounting plate.

29. The apparatus of claim 28, further comprising:
   a first plurality of needles having a common electrical connection, each of said first plurality of needles being secured in one of said plate holes of said first mounting plate, a first end of each capillary tube being associated with one needle in said first mounting plate.

30. The apparatus of claim 29, wherein
   said array of plate holes in said first mounting plate is rectangular, having 8 rows and 12 columns, and dimensions of less than 7.5 cm×11.0 cm.

31. An apparatus for use in capillary electrophoresis comprising:
   a first mounting plate having a first side and a second side; and
   a plurality of capillary tubes, each having first and second capillary ends, each capillary tube being fixed to said mounting plate, said first capillary end projecting on said first mounting plate first side, wherein
   centers of said projecting first capillary ends are spaced apart from one another, forming a two-dimensional array of first capillary ends, said array of first capillary ends having a spatial arrangement corresponding to that of an array of wells associated with a microtitre tray.

32. An apparatus for simultaneously performing capillary gel electrophoresis in a plurality of capillaries, said apparatus comprising:
   a capillary device comprising:
      a first mounting plate having a first side and a second side; and
      a plurality of capillary tubes, each having first and second capillary ends, each capillary tube being fixed to said mounting plate, said first capillary end projecting on said first mounting plate first side, wherein centers of said projecting first capillary ends are spaced apart from one another, forming a two-dimensional array of first capillary ends, said array of first capillary ends having a spatial arrangement corresponding to that of an array of wells associated with a microtitre tray;

means for simultaneously immersing said first capillary ends into samples present in an array of wells of a microtitre tray and introducing a portion of said samples into said first capillary ends; and means for simultaneously applying a voltage difference between the first ends of the capillaries and their respective second ends.

33. A method for simultaneously performing capillary gel electrophoresis in a plurality of capillaries, comprising the steps of:

providing a capillary tube holding apparatus wherein first ends of said capillaries are arranged into an array having a spatial arrangement corresponding to that of an array of wells associated with a microtitre tray;

simultaneously immersing said first ends into samples present in said array of wells and introducing a portion of said samples into said first capillary ends; and simultaneously applying a voltage difference between the first ends of the capillaries and their respective second ends.

34. The apparatus according to any one of claims 1, 8, 20, 31 and 32, wherein said two-dimensional array of first capillary ends comprises at least 8 rows and 12 columns.

35. The apparatus according to claim 34, wherein said two-dimensional array of first capillary ends comprises 16 rows and 24 columns.

* * * * *